United States Patent [19]

Rose et al.

[11] Patent Number: 5,893,371
[45] Date of Patent: Apr. 13, 1999

[54] NON-NICOTINE SMOKING CESSATION AID

[75] Inventors: Jed E. Rose; Frederique M. Behm, both of Durham, N.C.

[73] Assignee: Duke University, Durham, N.C.

[21] Appl. No.: 08/309,790

[22] Filed: Sep. 21, 1994

Related U.S. Application Data

[63] Continuation-in-part of application No. 07/979,804, Nov. 20, 1992, abandoned.

[51] Int. Cl.$^6$ .................................................. A24F 47/00
[52] U.S. Cl. .................................................. 131/270
[58] Field of Search .................................. 131/270, 273, 131/347, 352, 359

[56] References Cited

U.S. PATENT DOCUMENTS

| | | | |
|---|---|---|---|
| 4,284,089 | 8/1981 | Ray | 131/270 |
| 4,715,387 | 12/1987 | Rose | 131/270 |
| 4,800,903 | 1/1989 | Ray et al. | 131/273 |
| 4,846,199 | 7/1989 | Rose | 131/329 |
| 4,887,620 | 12/1989 | Summers | 131/352 |
| 4,920,989 | 5/1990 | Rose et al. | 131/270 |
| 4,945,928 | 8/1990 | Rose | 131/270 |
| 4,953,572 | 9/1990 | Rose et al. | 131/270 |
| 5,016,652 | 5/1991 | Rose et al. | 131/270 |

FOREIGN PATENT DOCUMENTS

| | | | |
|---|---|---|---|
| 929529 | 6/1963 | United Kingdom | 131/270 |

OTHER PUBLICATIONS

J. Leffingwell et al., *Tobacco Flavoring for Smoking Products* (1972) (R.J. Reynolds Tobacco Co., Winston–Salem, NC).

Jed E. Rose et al., "Sensory Blockade of Smoking Satisfaction", *Pharmacology Biochemistry & Behavior*, 23 (Dec. 1985) pp. 289–293.

Jed E. Rose and Carol S. Hickman, "Citric Acid Aerosol as a Potential Smoking Cessation Aid", *Chest*, 92 (Dec. 1987) pp. 1005–1008.

Jed. E. Rose, "The Role of Upper Airway Stimulation in Smoking", *Nicotine Replacement: A Critical Evaluation* (Dec. 1988) (Alan R. Liss, Inc.), pp. 95–106.

Edward D. Levin et al., "Development of a citric acid aerosol as a smoking cessation aid", *Drug and Alcohol Dependence*, 25 (Dec. 1990) pp. 273–279.

Edward D. Levin et al., "The use of flavor in cigarette substitutes", *Drug and Alcohol Dependence*, 26 (Dec. 1990) pp. 155–160.

Frederique M. Behm, et al., "Low–Nicotine Regenerated Smoke Aerosol Reduces Desire for Cigarettes", *Journal of Substance Abuse*, 2 (1990) pp. 237–247.

Jed E. Rose and Edward D. Levin, "Inter–relationships between conditioned and primary reinforcement in the maintenance of cigarette smoking", *British Journal of Addiction*, 86 (Dec. 1991) pp. 605–609.

Fuller et al., "Bronchoconstrictor Response to Inhaled Capsaicin in Humans", *American Physiological Society*, pp. 1080–1084 (Nov., 1984).

*Primary Examiner*—William H. Grieb
*Attorney, Agent, or Firm*—Jenkins & Wilson, P.A.

[57] ABSTRACT

A non-nicotine method and apparatus for use to reduce the need to smoke tobacco and which utilizes one or more constituents from black pepper or red pepper which are introduced into the user's respiratory tract by inhalation from either a vapor delivery system or an aerosol delivery system. Subsequent to inhalation, the constituents from black pepper or red pepper create respiratory tract sensations similar to those created by tobacco smoke and thereby serve to reduce the need to smoke tobacco. The one or more constituents from black and/or red pepper include essential oils of black and/or red pepper as well as pepper irritants including capsaicin, piperine and phellandrene.

21 Claims, 4 Drawing Sheets

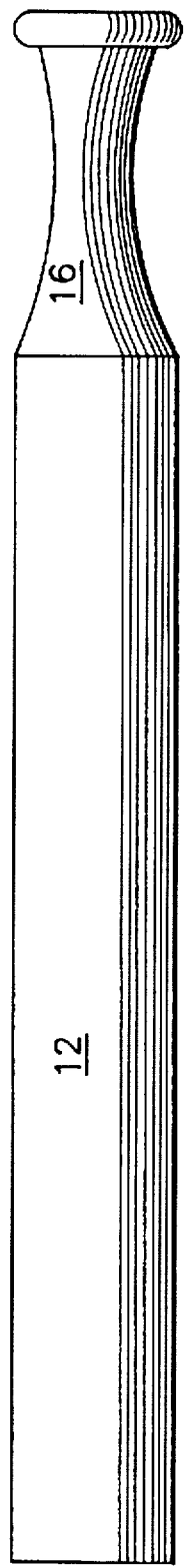
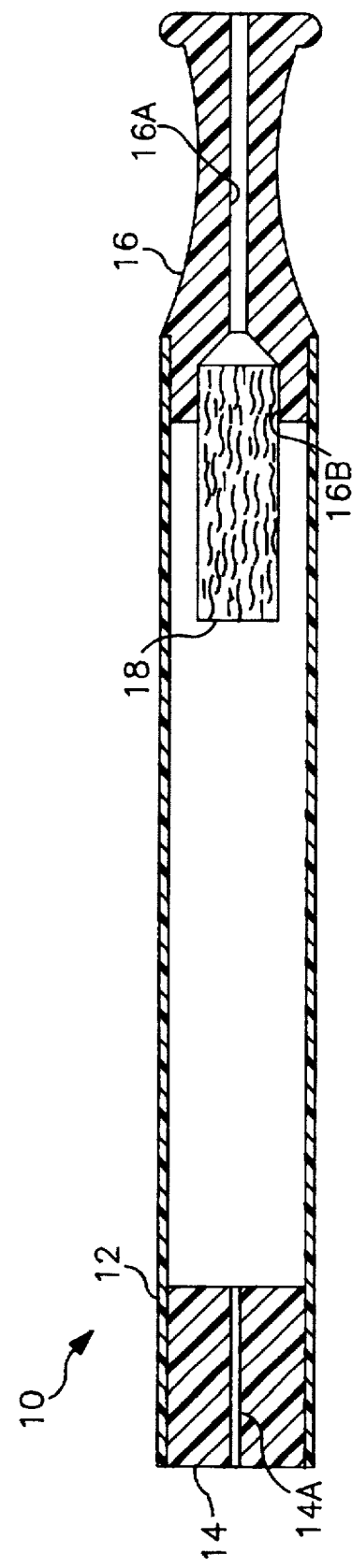

NON-NICOTINE SMOKING CESSATION AID

This is a continuation-in-part of application Ser. No. 07/979,804 filed on Nov. 20, 1992, now abandoned.

GOVERNMENT RIGHTS

This invention was made with U.S. government support by virtue of the material support of the Veterans Administration. The government has certain rights in the invention.

TECHNICAL FIELD

The present invention relates in general to a smoking cessation aid, and more particularly to a non-nicotine smoking cessation aid which uses one or more constituents from black and/or red pepper to simulate sensations in the respiratory tract which would normally be caused by tobacco smoke in order to reduce the need of the user to smoke tobacco.

RELATED ART

With the increasing recognition of the health hazards associated with cigarette smoking, increasing attention has been focused on less harmful means to provide some of the same satisfaction obtained by smoking. Some of the methods rely on nicotine replacement through nicotine chewing gum, nicotine skin patches or nicotine nasal sprays. Research conducted over the last 12 years by applicants has explored the role of nicotine as a reinforcer for smoking and has investigated the efficacy of nicotine replacement as an aid to smoking cessation.

While it is clear from applicants' work and that of others that nicotine replacement can facilitate smoking cessation by providing some relief for certain withdrawal symptoms, such as irritability and difficulty concentrating, it is equally clear that subjective craving for cigarettes is not effectively relieved by the pharmacologic effects of nicotine alone. An analogy can be drawn to hunger and food consumption, in which intravenous or intragastric feeding is not nearly as satisfying as eating a meal.

With smoking, the sensations experienced in the respiratory tract upon inhalation of each puff of smoke, along with the taste and aroma of the smoke and the act of puffing, provide a considerable portion of the satisfaction a smoker experiences. It is believed that these sensory cues may help to maintain a dependency on cigarettes. In experiments in which applicants temporarily blocked the respiratory tract sensations of smoking by having subjects inhale a lidocaine aerosol, it was found that the satisfaction associated with inhalation of a controlled dose of nicotine was significantly reduced. Thus, applicants have attempted to develop a smoking cessation aid which delivers some of the sensory and habit aspects of smoking.

One such technique that has been developed is a method of delivering fine particles of citric acid or related compounds to simulate the respiratory tract sensations of smoking (see U.S. Pat. No. 4,715,387). Applicants have found the device to be helpful in relieving smokers' craving for cigarettes. Until the invention described hereinbelow was developed, the citric acid invention has been the only method for simulating respiratory tract sensations of smoking without using nicotine or other drugs that entail extensive FDA regulation and which may be addictive.

Some other methods for providing the sensory components of smoking which do involve the use of nicotine include a low-dose nicotine aerosol (see U.S. Pat. No. 4,953,572), a regenerated smoke aerosol (see U.S. Pat. No. 4,945,928), and a nicotine vapor inhaler (see U.S. Pat. No. 4,284,089). These methods, while showing promise, suffer from several shortcomings. First, nicotine, when delivered apart from cigarettes, is classified as a drug and is subject to extensive FDA regulation which imposes considerable costs on product development, and thereby often discourages potential licensees. Second, nicotine is viewed as an addictive drug, and even if low doses are used, the approach may be psychologically unappealing to smokers who want to be freed from all dependence on nicotine. Finally, nicotine has an aversive bitter, burning taste, which limits the acceptability of products such as nicotine chewing gum. Even smokers usually do not like the taste of nicotine when "unmasked" by being dissociated from other flavorful smoke components.

The regenerated smoke aerosol method might overcome the regulatory problems because pure nicotine is not used, and many of the desired taste components of tar are still present to provide some masking of the undesirable properties of nicotine. However, the apparatus and technology required is complex and the method involves "smoking", thereby rendering it objectionable to those individuals who want to quit smoking completely.

The present non-nicotine smoking cessation aid invention overcomes the problems of previous smoking cessation aids described above and possesses unexpected and surprising efficacy in use.

DISCLOSURE OF THE INVENTION

In accordance with the present invention, a method is provided for reducing the incidence of tobacco smoking by simulating respiratory tract sensations in a user substantively similar to those obtained by inhalation of tobacco smoke. The method comprises providing one or more constituents from black and/or red pepper in a device adapted for introduction into the user's mouth and for inhalation therefrom by the user, and then inhaling from the device so as to introduce at least a portion of the constituents from black and/or red pepper to the respiratory tract. In this fashion, the respiratory tract sensations created by the constituents from black and/or red pepper simulate those created by tobacco smoke so as to reduce the need of the user to smoke tobacco.

Also, the present invention provides a method for reducing the incidence of tobacco smoking by simulating respiratory tract sensations in a user substantively similar to those obtained by inhalation of tobacco smoke, said method comprising: (a) providing an irritant selected from the group consisting of one or more constituents from black and/or red pepper, capsaicinoids, and mixtures of the foregoing in a device adapted for introduction into the user's mouth and for inhalation therefrom by the user; (b) inhaling from said device so as to introduce at least a portion of said irritant to the respiratory tract of the user; and (c) periodically repeating step (b); whereby the respiratory tract sensations created by said irritant are sufficient to simulate those created by tobacco smoke to reduce the need of the user to smoke tobacco, but insufficient to create a gross bronchoconstrictor response in the user.

Furthermore, the present invention provides a device for reducing the incidence of tobacco smoking by simulating respiratory tract sensations in a user substantively similar to those obtained by inhalation of tobacco smoke, said device comprising a housing including therein an irritant selected from the group consisting of one or more constituents from black and/or red pepper, capsaicinoids and mixtures of the foregoing dissolved in a liquid carrier and present in an amount sufficient to simulate the sensations in the upper respiratory tract caused by tobacco smoke, said device being adapted for periodic introduction into the user's mouth and for inhalation therefrom to introduce periodically at least a portion of said irritant to the respiratory tract of the user; whereby the respiratory tract sensations created by said irritant are sufficient to simulate those created by tobacco smoke to reduce the need of the user to smoke tobacco but insufficient to create a gross bronchoconstrictor response in the user.

It is therefore one of the primary objects of the present invention to provide a method of aiding in the reduction of the incidence of tobacco smoking by orally introducing one or more constituents from black and/or red pepper to the respiratory tract to simulate the sensations in the respiratory tract normally caused by tobacco smoke.

It is another object of the present invention to provide a method of aiding in the reduction of the incidence of tobacco smoking in which one or more constituents from black and/or red pepper are periodically administered to the respiratory tract of an individual desiring to cease smoking to thereby simulate the sensation created by tobacco smoke and to consequently replace the need for the individual to smoke tobacco.

It is a further object of the present invention to provide a method of aiding in the reduction of incidence of tobacco smoking by use of a vapor which contains one or more constituents from black and/or red pepper.

It is yet another object of the present invention to provide a method of aiding in the reduction of incidence of tobacco smoking by use of an aerosol which contains one or more constituents from black and/or red pepper.

It is still another object of the present invention to provide a device to aid in the reduction of incidence of tobacco smoking and which comprises means for orally introducing one or more constituents from black and/or red pepper to the respiratory tract that are capable of simulating the sensations therein normally caused by tobacco smoke so as to reduce the need of an individual to smoke tobacco.

Some of the objects of the invention having been stated hereinabove, other objects will become evident as the description proceeds, when taken in connection with the accompanying drawings as best described hereinbelow.

BRIEF DESCRIPTION OF THE DRAWINGS

FIG. 1 is a side elevation view of a first embodiment of a device in accordance with the invention for oral administration of a vapor comprising one or more constituents from black and/or red pepper;

FIG. 2 is a vertical cross-sectional view of the device shown in FIG. 1;

BEST MODE FOR CARRYING OUT THE INVENTION

The present invention provides a new and surprisingly effective method and device for delivering respiratory tract sensations of smoking to give at least partial relief of the craving for cigarettes and wherein no nicotine or smoke components are required.

A first embodiment of the invention is shown in FIGS. 1 and 2 and uses a cigarette-sized tube containing a cartridge which is preferably saturated with essential oil of black pepper to deliver a vapor when a smoker puffs on the device and inhales. The invention has advantages over prior art such as the citric acid aerosol invention discussed hereinabove. First, the pepper vapor does not have the sour taste of citric acid or related acids, and hence may be preferred by many individuals for that reason. Second, it is likely that constituents of pepper stimulate the same nerve endings (vagal C-fibers) in the respiratory tract that are stimulated by nicotine. In contrast, citric acid is believed to stimulate a different population of irritant receptors.

Applicants believe that pepper constituents provide a different, and for some individuals, a better simulation of the qualitative aspects of smoking-related respiratory tract sensations than do citric acid or other agents used in the prior art and, because it does not contain any nicotine, avoids the disadvantages of well-known nicotine replacement techniques.

Figure 3:
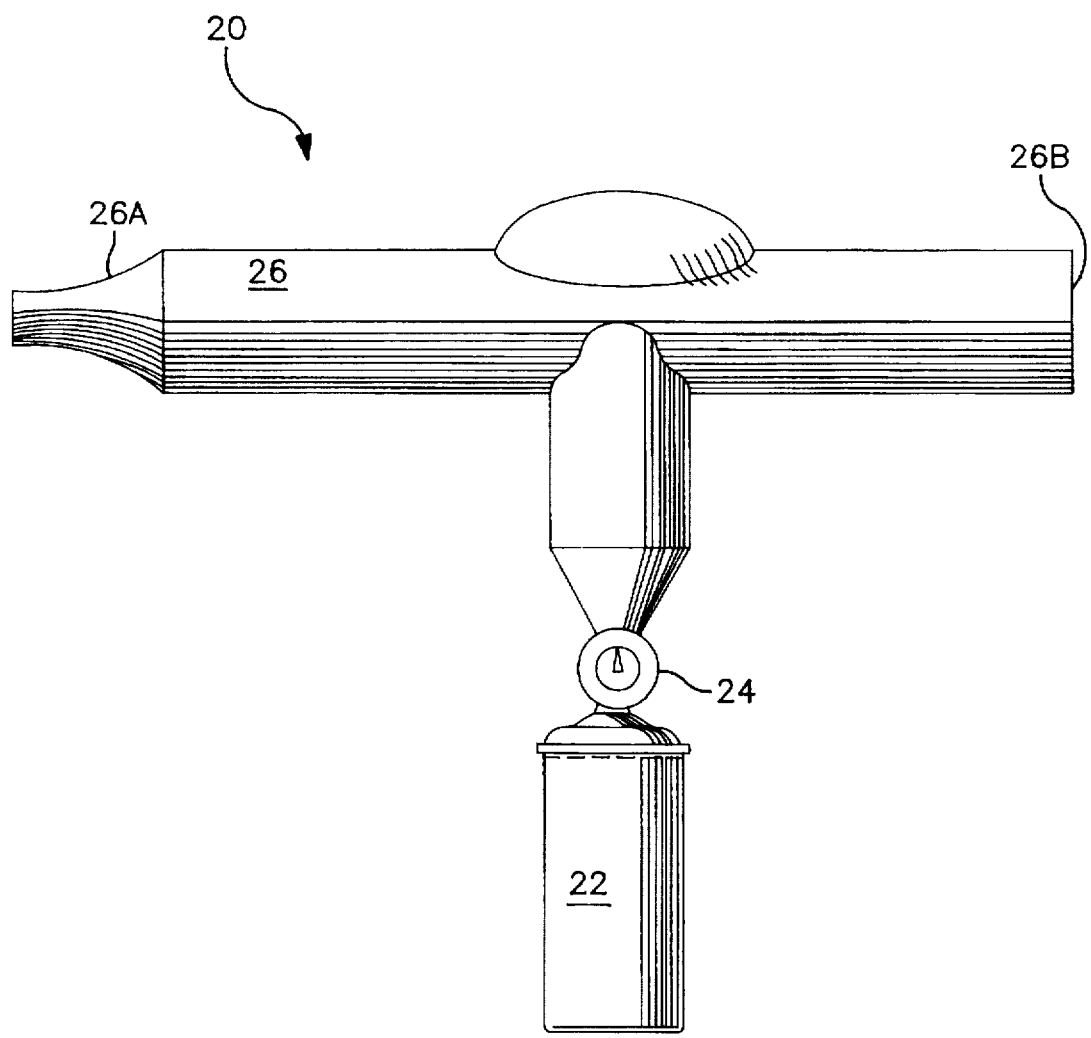
FIG. 3 is a side elevation view of a second embodiment of a device in accordance with the present invention for oral administration of an aerosol comprising one or more constituents from black and/or red pepper.
Figure 4:
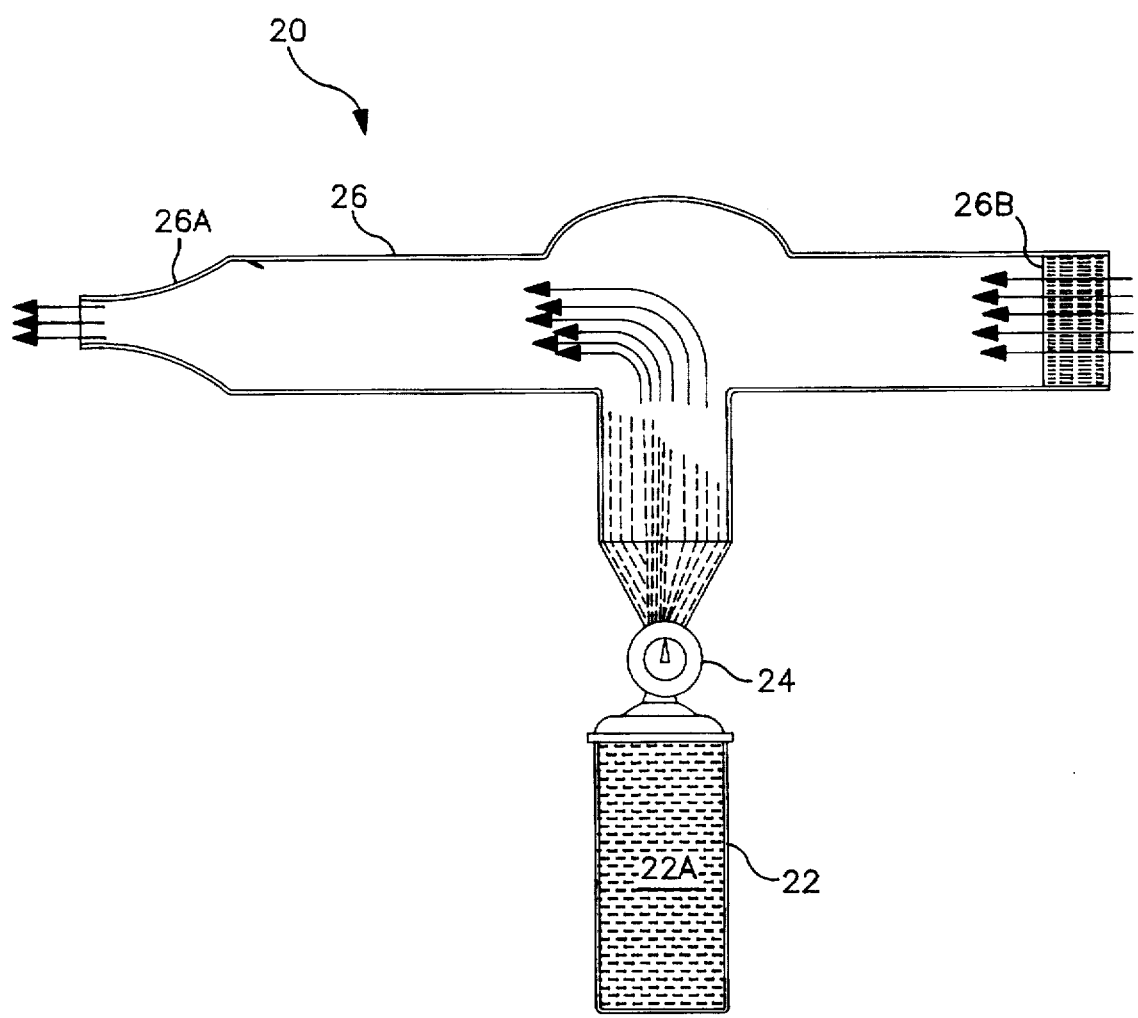
FIG. 4 is a vertical cross-sectional view of the device shown in FIG. 3.

Although applicant contemplates that the method of the present invention can be practiced with a number of different devices, a preferred vapor device 10 is shown in FIGS. 1 and 2 and a preferred aerosol spray device 20 is shown in FIGS. 3 and 4 Vapor device 10 comprises an elongate tube 12, preferably formed from plastic or a similar type of material. Tube 12 is provided with plug 14 at one end thereof which also is most suitably formed of plastic. Plug 14 defines a central aperture 14A therethrough so as to allow for inhalation through vapor device 10 by the user thereof. Tube 12 is provided with mouthpiece 16 at the other end thereof which defines an air passageway aperture 16A therethrough.

Also, and very importantly to the invention, mouthpiece 16 is provided with an enlarged chamber 16B which is defined within the inside face thereof and sized so as to engage at least a portion of cartridge 18 therein as best seen in FIG. 1. Cartridge 18, most suitably formed from a fibrous mass such as cigarette filter tow or the like, is saturated with the aforementioned essential oil of black pepper, although essential oil of red pepper and other constituents of black and/or red pepper may be used in practicing the present invention and are contemplated as being within the scope of the present invention as will be described hereinbelow.

Specific irritants in black pepper, including piperine and phellandrene, may be used in vapor delivery device 10 to increase the intensity of sensory impact relative to that obtained when using the black pepper essential oil. Also, and more broadly, essential oil or oleoresin of red pepper and irritating components of black pepper and/or red pepper may be used in vapor delivery device 10. However, in order to deliver nonvolatile pepper constituents such as the red pepper active ingredient, capsaicin, the constituent most suitably should be dissolved in a suitable solvent such as ethanol (at about 1.0 to 10.0 weight percent) or, in the alternative, an aerosol delivery system 20 such as shown in FIGS. 3 and 4 (described below) may be used. Means for applying heat to cartridge 18, such as a miniature battery-operated coil (not shown), could also be used to facilitate delivery of capsaicin vapor by device 10.

As best seen in FIGS. 3 and 4, an aerosol delivery system 20 is shown which is particularly adapted for delivering nonvolatile constituents of black and/or red pepper, such as capsaicin, although applicant believes as stated above that these nonvolatile pepper constituents can also be properly delivered by device 10 if dissolved in a suitable solvent. Moreover, although lending itself well to delivery of nonvolatile pepper constituents, aerosol delivery system device 20 can be used for the delivery of both nonvolatile as well as volatile pepper constituents when oleoresins of black and/or red pepper are dissolved in a liquid carrier such as ethanol or propylene glycol (at about 0.01 to 0.10 weight percent), other volatile constituents are dissolved in a liquid carrier such as ethanol or propylene glycol (at about 0.10 to 1.0 weight percent) and nonvolatile constituents (e.g., capsaicin) are dissolved in a liquid carrier such as ethanol or propylene glycol (at about 0.0002 to 0.005 weight percent).

It should be appreciated that the specific liquid carriers and weight percents set forth above are only representative examples and are not intended to limit the scope of the invention.

Although aerosol delivery system device 20 may be made in many different embodiments, representative embodiment 20 as shown in FIGS. 3 and 4 generally comprises a container 22 which has a solution of one or more constituents from black and/or red pepper dissolved in a suitable liquid carrier therein (shown as 22A). A valve 24 is provided at the upper end of container 22 and may be of any conventional form (such as a push-button valve) which can be actuated by a user in order to dispense a solution containing one or more pepper constituents from container 22 upon opening of valve 24. An elongate housing 26 is positioned above valve 24 and in fluid communication therewith. Housing 26, most suitably in the form of an inhalation tube, defines a mouthpiece 26A at one end for introduction into a user's mouth and a screen 26B in the other end thereof to remove any foreign particles from the airstream flowing through housing 26 during inhalation by a user.

Container 22 is most suitably a pressurized container containing, in addition to the pepper constituent solution 22A, an inert gas under pressure. Various types of inert gases such as are conventional and well-known in the pressurized container field may be employed in container 22.

The aerosol spray dispensed by aerosol delivery system 20 contains a sufficient amount of essential oil of black pepper and/or essential oil of red pepper or one or more other constituents from black and/or red pepper to simulate the sensations created by tobacco smoke in the upper respiratory tract so as to avoid the need of tobacco smoke to create the sensations.

Thus, it can be appreciated that essential oil or oleoresin of black pepper, essential oil or oleoresin of red pepper, as well as selected specific irritants in black and red pepper such as piperine, phellandrene and capsaicin may be used in either vapor delivery system 10 or aerosol delivery system 20 described above. Vapor delivery system device 10 lends itself better to the use of essential oil of black pepper, oleoresin of red pepper or volatile irritants in black and/or red pepper such as phellandrene. However, as described above, the nonvolatile irritant capsaicin could also be used in device 10 if dissolved in a suitable solvent. Device 20 lends itself particularly well to dispensing nonvolatile irritants in black or red pepper such as capsaicin. However, aerosol delivery system device 20 can also serve to dispense essential oil of black pepper, oleoresin of red pepper and volatile irritants in black and/or red pepper when dissolved in a suitable carrier as described hereinabove.

Although the method and device of the instant invention primarily contemplate the use of irritants comprising constituents of black and/or red pepper, applicants further believe that capsaicinoids possess significant efficacy when used as the irritant therein and therefore are also contemplated to be within the scope of the invention. As will be appreciated by one skilled in the art, both naturally occurring capsaicinoids and synthetic capsaicinoids having the same pharmacological effect as naturally occurring capsaicinoids may be used in the practice of the present invention.

Laboratory Test Results

To test the efficacy of the instant invention, applicants conducted a controlled laboratory study in which 48 subject smokers were randomly subjected to one of three conditions: (1) a placebo cigarette substitute consisting of a cigarette-size tube with an unflavored cartridge therein; (2) essential oil of black pepper contained in a cartridge inserted into the same cigarette-size tube; and (3) a mint/menthol cartridge used in the same cigarette-size tube (which is marketed as a commercial smoking cessation product under the trademark E-Z QUIT).

Subjects in each condition puffed on the cigarette substitute freely for a three-hour period. Smoking was not permitted during the study, and the subjects arrived at the laboratory after eight hours abstinence from smoking (confirmed by expired air carbon monoxide analysis). Subsequent to the test, the subjects were asked to rate the sensory qualities of the device and also to rate their craving for cigarettes and other smoking withdrawal symptoms experienced over the three hours.

Figure 5:
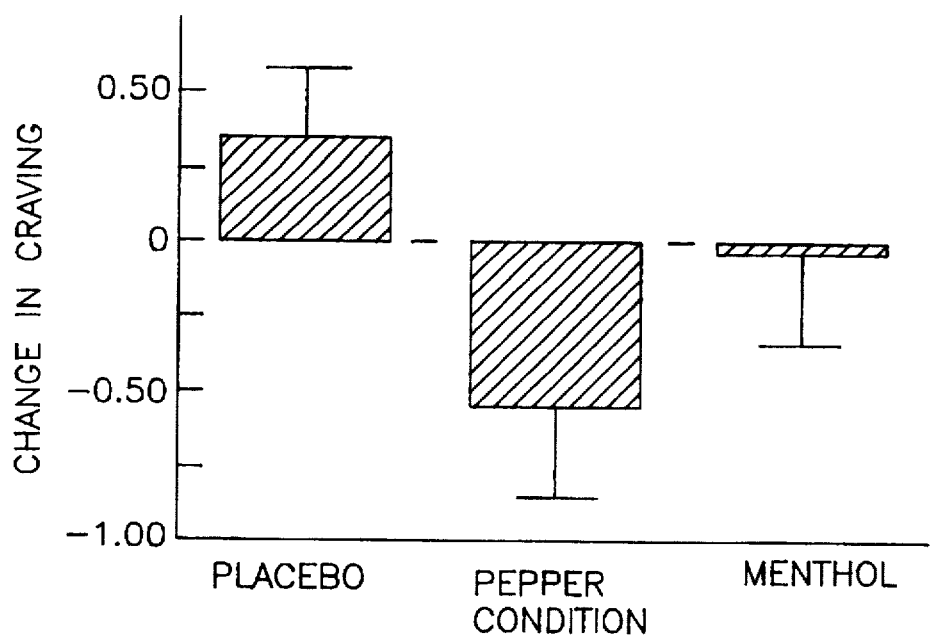
FIG. 5 is a graph showing the reported change in craving for tobacco smoke after puffing for a predetermined time on a vapor device including a cartridge saturated with essential oil of black pepper in accordance with the present invention, as compared to a placebo cigarette substitute and a commercial smoking cessation product utilizing a mint/menthol cartridge.
Figure 6:
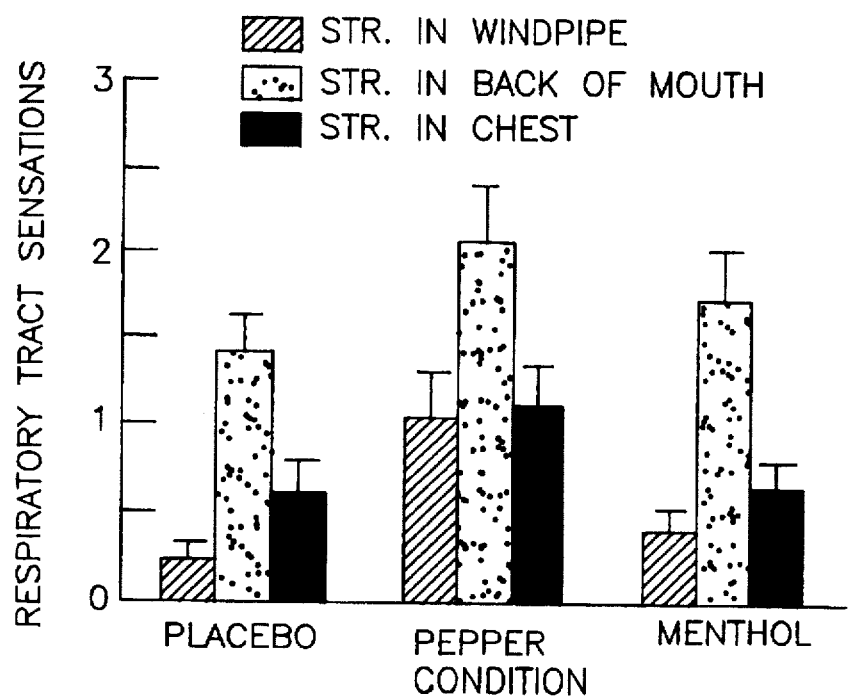
FIG. 6 is a graph showing subjective ratings of respiratory tract sensations after puffing for a predetermined time on the three devices described in FIG. 5.

As shown in FIG. 5 of the drawings below wherein the change in craving is measured in units on a scale ranging from 1 (very definitely not) to 7 (very definitely), the craving for cigarettes tended to increase over the three hours in the placebo condition while decreasing in the pepper condition, the difference between these two conditions being significant ($p<0.05$). There was little change attributable to the E-Z QUIT mint/menthol device, which did not differ significantly from the placebo. Subjective ratings of respiratory tract sensations also showed that the pepper condition was rated as more intense than the other two conditions (see FIG. 6). No subject reported a gross bronchoconstriction response.

These results support applicants' belief that pepper components and other irritants described herein may be useful in alleviating the desire to smoke and thereby facilitating smoking cessation.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for reducing the incidence of tobacco smoking by simulating respiratory tract sensations in a user substantively similar to those obtained by inhalation of tobacco smoke, said method comprising:

(a) providing an irritant selected from the group consisting of one or more constituents from black and/or red pepper, capsaicinoids, and mixtures of the foregoing in a device adapted for introduction into the user's mouth and for inhalation therefrom by the user; and (b) inhaling from said device so as to introduce at least a portion of said irritant to the respiratory tract; and (c) periodically repeating (b), whereby the respiratory tract sensations created by said irritant simulate those created by tobacco smoke to reduce the need of the user to smoke tobacco.

2. A method according to claim 1 further characterized in that said method comprises inhaling from said device wherein said device comprises a tube substantially similar in size to a cigarette and having a cartridge therein saturated with a solution comprising said irritant so that a vapor containing said irritant is introduced to the respiratory tract of the user.

3. A method according to claim 2 further characterized in that said cartridge is saturated with a solution comprising essential oils and/or oleoresins of black and/or red pepper.

4. A method according to claim 2 further characterized in that said cartridge is saturated with a solution comprising said one or more constituents from black and/or red pepper wherein said one or more constituents is selected from the group consisting of capsaicin, piperine, phellandrene and mixtures of the foregoing.

5. A method according to claim 1 further characterized in that said method comprises inhaling from said device wherein said device comprises aerosol delivery means having a solution comprising said irritant therein so that an aerosol spray containing said irritant is introduced to the respiratory tract of the user.

6. A method according to claim 5 further characterized in that said solution within said aerosol delivery means comprises essential oils and/or oleoresins of black and/or red pepper.

7. A method according to claim 5 further characterized in that said solution within said aerosol delivery means comprises said one or more constituents of black and/or red pepper wherein said one or more constituents is selected from the group consisting of capsaicin, piperine, phellandrene and mixtures of the foregoing.

8. A method for reducing the incidence of tobacco smoking by simulating respiratory tract sensations in a user substantively similar to those obtained by inhalation of tobacco smoke, said method comprising:

(a) providing an irritant selected from the group consisting of one or more constituents from black and/or red pepper, capsaicinoids, and mixtures of the foregoing in a device adapted for introduction into the user's mouth and for inhalation therefrom by the user;

(b) inhaling from said device so as to introduce at least a portion of said irritant to the respiratory tract of the user; and (c) periodically repeating step (b); whereby the respiratory tract sensations treated by said irritant are sufficient to simulate those created by tobacco smoke to reduce the need of the user to smoke tobacco, but insufficient to create a gross bronchoconstrictor response in the user.

9. A device for reducing the incidence of tobacco smoking by simulating respiratory tract sensations in a user substantively similar to those obtained by inhalation of tobacco smoke, said device comprising a housing including therein an irritant selected from the group consisting of one or more constituents from black and/or red pepper, capsaicinoids and mixtures of the foregoing dissolved in a liquid carrier and present in an amount sufficient to simulate the sensations in the upper respiratory tract caused by tobacco smoke, said device being adapted for periodic introduction into the user's mouth and for inhalation therefrom to introduce periodically at least a portion of said irritant to the respiratory tract of the user; whereby the respiratory tract sensations created by said irritant are sufficient to simulate those created by tobacco smoke to reduce the need of the user to smoke tobacco but insufficient to create a gross bronchoconstrictor response in the user.

10. A method according to claim 8 further characterized in that said method comprises inhaling from said device wherein said device comprises a tube substantially similar in size to a cigarette and having a cartridge therein saturated with a solution comprising said irritant so that a vapor containing said irritant is introduced to the respiratory tract of the user.

11. A method according to claim 10 further characterized in that said cartridge is saturated with a solution comprising essential oils and/or oleoresins of black and/or red pepper.

12. A method according to claim 10 further characterized in that said cartridge is saturated with a solution comprising said one or more constituents from black and/or red pepper wherein said one or more constituents is selected from the group consisting of capsaicin, piperine, phellandrene and mixtures of the foregoing.

13. A method according to claim 8 further characterized in that said method comprises inhaling from said device wherein said device comprises aerosol delivery means having a solution comprising said irritant therein so that an aerosol spray containing said irritant is introduced to the respiratory tract of the user.

14. A method according to claim 13 further characterized in that said solution within said aerosol delivery means comprises essential oils and/or oleoresins of black and/or red pepper.

15. A method according to claim 13 further characterized in that said solution within said aerosol delivery means comprises said one or more constituents of black and/or red pepper wherein said one or more constituents is selected from the group consisting of capsaicin, piperine, phellandrene and mixtures of the foregoing.

16. A device according to claim 9 further characterized in that said device comprises a tube substantially similar in size to a cigarette and having a cartridge therein saturated with a solution comprising said irritant so that inhalation through said tube introduces a vapor containing said irritant to the respiratory tract of the user.

17. A device according to claim 16 further characterized in that said cartridge is saturated with a solution comprising essential oils and/or oleoresins of black and/or red pepper.

18. A device according to claim 16 further characterized in that said cartridge is saturated with a solution comprising said one or more constituents from black and/or red pepper wherein said one or more constituents is selected from the group consisting of capsaicin, piperine, phellandrene and mixtures of the foregoing.

19. A device according to claim 9 further characterized in that said device comprises aerosol delivery means having a solution comprising said irritant therein so that inhalation through said aerosol delivery means introduces an aerosol spray containing said irritant to the respiratory tract of the user.

20. A device according to claim 19 further characterized in that said solution within said aerosol delivery means comprises essential oils and/or oleoresins of black and/or red pepper.

21. A device according to claim 19 further characterized in that said solution within said aerosol delivery means comprises said one or more constituents of black and/or red pepper wherein said one or more constituents is selected from the group consisting of capsaicin, piperine, phellandrene and mixtures of the foregoing.

* * * * *